United States Patent [19]

Bezwada et al.

[11] Patent Number: 4,643,191

[45] Date of Patent: Feb. 17, 1987

[54] CRYSTALLINE COPOLYMERS OF P-DIOXANONE AND LACTIDE AND SURGICAL DEVICES MADE THEREFROM

[75] Inventors: Rao S. Bezwada, Whitehouse Station; Shalaby W. Shalaby, Lebanon; Hugh Newman, Jr., Chester; Adel Kafrawy, Flemington, all of N.J.

[73] Assignee: Ethicon, Inc., Somerville, N.J.

[21] Appl. No.: 802,546

[22] Filed: Nov. 29, 1985

[51] Int. Cl.$^4$ .............................................. C08G 63/08
[52] U.S. Cl. .............................. 128/335.5; 128/334 R; 525/411; 525/415; 528/354
[58] Field of Search ................ 528/354; 525/411, 415; 128/335.5

[56] References Cited

U.S. PATENT DOCUMENTS

| | | | |
|---|---|---|---|
| 4,052,988 | 10/1977 | Doddi et al. | 528/354 |
| 4,137,921 | 2/1979 | Okuzumi et al. | 525/411 X |
| 4,157,437 | 6/1979 | Okuzumi et al. | 525/415 X |
| 4,243,775 | 1/1981 | Rosensaft et al. | 528/354 X |
| 4,300,565 | 11/1981 | Rosensaft et al. | 525/415 X |
| 4,470,416 | 9/1984 | Kafrawy et al. | 528/354 X |
| 4,591,630 | 5/1986 | Gertzman et al. | 528/354 X |

*Primary Examiner*—Earl Nielsen
*Attorney, Agent, or Firm*—Charles J. Metz

[57] ABSTRACT

A crystalline copolymer is produced by first polymerizing p-dioxanone to form a mixture of monomer and homopolymer, and then adding lactide to this mixture and polymerizing to form a copolymer.

16 Claims, No Drawings

CRYSTALLINE COPOLYMERS OF P-DIOXANONE AND LACTIDE AND SURGICAL DEVICES MADE THEREFROM

The invention relates to crystalline copolymers of p-dioxanone and lactide, a process for making said copolymers, and to surgical devices such as high pliability monofilament sutures and ligatures made therefrom.

BACKGROUND OF THE INVENTION

Surgical devices, in particular absorbable monofilament sutures and ligatures and hemostatic ligating clips, made from p-dioxanone homopolymer are valuable commercial articles. This invention is directed to a means for providing p-dioxanone polymers that have properties that are different from those that can be obtained in the homopolymer. This invention thereby provides a means for extending the utility of p-dioxanone polymers.

P-dioxanone polymers are disclosed by Doddi et al. in U.S. Pat. No. 4,052,988, who also disclose and claim sutures and other surgical devices made from such polymers. In the paragraph bridging Columns 8 and 9 of the Doddi et al. patent, it is disclosed that lactide may be copolymerized with p-dioxanone to produce absorbable sutures.

Surgical filaments such as sutures and ligatures of p-dioxanone homopolymer are commercially available in the form of monofilaments. One of the desirable characteristics of a monofilament suture is to exhibit a combination of high strength (in the form of straight tensile and knot tensile strength) and good pliability. Monofilaments of p-dioxanone homopolymers are perceived by the surgeon as being rather stiff. One of the valuable advantages of this invention is that it provides p-dioxanone polymers that are more pliable and, in many cases, stronger than p-dioxanone homopolymer, thereby substantially enhancing the utility of p-dioxanone polymers.

BRIEF SUMMARY OF THE INVENTION

The polymers of the invention are certain copolymers of p-dioxanone and lactide, the predominant portion of the copolymers being polymerized p-dioxanone with the remainder being polymerized lactide. The invention also provides sterilizable surgical devices made from these copolymers, preferably monofilament sutures and ligatures that have a desirable combination of high strength and excellent pliability (in part as exhibited by low Young's modulus). Other surgical devices are also provided by the invention. Illustrations include parts of surgical staples, small diameter tubes such as those that are used as sheaths to protect nerve and small vessel anastomoses, fabrics including woven or knitted tubular fabrics, and the like.

The invention also provides a process for producing the segmented copolymers of the invention which comprises:

adding lactide to a mixture of p-dioxanone homopolymer and p-dioxanone monomer and subjecting the resulting reaction mixture to an elevated temperature for a period of time sufficient to produce a copolymer of p-dioxanone and lactide.

THE PRIOR ART

In addition to the Doddi et al. patent cited above (which is considered by Applicants to be the most relevant prior art), a number of other patents are relevant in that they disclose the production of absorbable copolymers by the sequential addition of monomers. These patents include Okuzumi et al., U.S. Pat. Nos. 4,137,921 and 4,157,437 and Rosensaft et al., U.S. Pat. Nos. 4,243,775 and 4,300,565.

DETAILED DESCRIPTION OF THE INVENTION

The most convenient way to carry out the process of the invention is to first carry out the melt polymerization of p-dioxanone monomer to produce a mixture of poly(p-dioxanone) homopolymer and p-dioxanone monomer, and without separating the monomer and polymer, use the resulting mixture in the process of the invention. This homopolymerization is carried out in the presence of a catalytically effective amount of a suitable metal-containing catalyst such as stannous octoate or stannous oxalate. Typical proportions of catalyst are found in monomer:catalyst molar ratios of from about 10,000:1 to about 60,000:1, and preferably from about 15,000:1 to about 40,000:1. The polymerization is carried out in the presence of an initiator such as an alkanol, a glycol, a hydroxyacid, or an amine. Specific illustrations of such initiators include 1-dodecanol, diethylene glycol, glycolic acid, lactic acid, ethanolamine, and the like. Typical proportions of the initiator are found in monomer:initiator molar ratios of from about 500:1 to about 1800:1. The polymerization of p-dioxanone is carried out at elevated temperatures under an inert atmosphere for a period of time sufficient to produce a mixture of p-dioxanone homopolymer and p-dioxanone monomer. Typical polymerization reaction temperatures are within the range of from about 100° C. to about 130° C., and is preferably about 110° C. The polymerization reaction is normally carried out until an equilibrium is reached between polymer and monomer. This is usually attained at about 15 to 30 weight percent monomer, based on weight of monomer plus polymer. Depending on the temperature and catalyst concentration, this reaction usually takes from about 4 to 8 hours. At the preferred temperature of about 110° C., the usual reaction time is 5 to 6 hours.

Lactide is then added to the mixture of p-dioxanone homopolymer and monomer, and the resulting reaction mixture is subjected to elevated temperature for a period of time sufficient to produce the copolymers of the invention. As a general rule, the reaction temperature for this polymerization will be within the range of from about 110° C. to about 160° C., and preferably from about 120° C. to about 140° C. At reaction temperatures within this range, the polymerization will be complete within a period of from about 1 to about 4 hours. The examples below illustrate specific reaction conditions.

The proportion of lactide that is added to the mixture of p-dioxanone homopolymer and monomer is usually from about 2 to about 30 weight percent and preferably from about 5 to about 20 weight percent, based on total weight of the reaction mixture (i.e., total weight of lactide, p-dioxanone homopolymer, and p-dioxanone monomer). The Examples below illustrate the production of the copolymers of the invention.

EXAMPLE 1

Preparation of Polydioxanone-melt/L(—)Lactide at 90/10 initial mole composition.

A flame dried, 250 milliliter, round bottom, three-neck flask was charged with 69.15 grams (0.6777 mole) of p-dioxanone, 0.1684 gram of 1-dodecanol, and 0.076 milliliter of stannous octoate (0.33 molar solution in toluene). The contents of the reaction flask were held under high vacuum at room temperature for about 16 hours. The flask was fitted with a flame dried mechanical stirrer and an adaptor with a hose connection. The reactor was purged with nitrogen three times before being vented with nitrogen. The reaction mixture was heated to 110° C. and maintained there for 5 hours. To the reaction flask, 10.85 grams (0.0753 mole) of L(—)lactide was added and the temperature was raised to 160° C. over the next 20 minutes. The bath temperature was maintained there for 2 hours. The temperature of the oil bath was lowered to 85° C. and maintained there for about 16 hours. The polymer was isolated, ground, and dried 48 hours/80° C./0.1 mm Hg. to remove any unreacted monomer. A weight loss of 14.8% was observed. The resulting polymer had a melting range of 96°–100° C. by hot stage microscopy, an inherent viscosity of 2.27 dl/g, and a crystallinity content of about 31% of X-ray diffraction. All inherent viscosity ("I.V.") values reported herein were measured at a concentration of 0.1 gram of polymer per deciliter of hexafluoroisopropyl alcohol, at 25° C. The molar ratio of PDO/PL (i.e., polymerized p-dioxanone/polymerized lactide) in the copolymer product was found to be 90.5/9.5 by NMR. (Since lactide is a cyclic dimer of two lactic acid units, as used herein, polymerized lactide also comprises two lactic acid units.)

EXAMPLE 2

Preparation of Polydioxanone-melt/L(—)Lactide at 80/20 initial mole composition.

A flame dried, 250 milliliter, round bottom, three-neck flask was charged with 59.12 grams (0.5794 mole) of p-dioxanone, 0.1620 gram of 1-dodecanol, and 0.0732 milliliter of stannous octoate (0.33 molar solution in toluene). The contents of the reaction flask were held under high vacuum at room temperature for about 16 hours. The flask was fitted with a flame dried mechanical stirrer and an adapter with a hose connection. The reactor was purged with nitrogen three times before being vented with nitrogen. The reaction mixture was heated to 110° C. and maintained there for 5 hours. To the reaction flask, 20.88 grams (0.1149 mole) and L(—)lactide was added and the temperature was raised to 160° C. over the next 20 minutes. The bath temperature was maintained there for 2 hours. The temperature of the oil bath was lowered to 85° C. and maintained there for about 16 hours. The polymer was isolated, ground, and dried 48 hours/80° C./0.1 mm Hg. to remove any unreacted monomer. A weight loss of 11.9% was observed. The resulting polymer had a melting range of 96°–99° C. by hot stage microscopy, an inherent viscosity of 2.53 dl/g, and a crystallinity content of about 24%. The molar ratio of PDO/PL in the polymer was found to be 82.4/17.6 by NMR.

Extrusion

In the preparation of fibers, especially surgical filaments, the copolymers are melt extruded through a spinnerette in a conventional manner to form one or more filaments, in accordance with the following general procedure used for laboratory scale experiments. Extrusion of the copolymers described herein was accomplished using an INSTRON Capillary Rheometer or a single screw extruder. The copolymers evaluated in the INSTRON Capillary Rheometer were packed in the preheated (80° to 90° C.) extrusion chamber and extruded through a 40 mil die (L/D=24.1) after a dwell time of 9 to 13 minutes at the extrusion temperature and a ram speed of 2 cm/min. While extrusion temperatures depend both on the polymer Tm and on the melt viscosity of the material at a given temperature, extrusion of the subject copolymers at temperatures of about 10° to 75° C. above the Tm is usually satisfactory. The extrusion temperatures of the example copolymers described herein ranged from 130° to 200° C. The extrudate typically was taken up through an ice water quench bath at 24 feet/minute, although other bath temperatures and take-up speeds occasionally were used.

The extrudate filaments (which have been allowed to cyrstallize sufficiently—usually, storage of the extruded filament at room temperature for 1 to 24 hours will suffice to permit the requisite crystallization to take place) are subsequently drawn about 6X to 7.5X in a one or multistage drawing process in order to achieve molecular orientation and improve tensile properties. The manner of drawing is as follows:

The extrudate (diameter range, usually 18–20 mils) passed through rollers at an input speed of four feet per minute and into a heated draw bath of glycerine. The temperatures of the draw bath can vary from about 25° to 90° C.; the examples described herein employ temperatures between 49° and 60° C. The draw ratio in this first stage of drawing can vary from 3X to about 7X; the examples described herein employ draw ratios from 4X to 6X. The partially drawn fibers are then placed over a second set of rollers into a glycerine bath (second stage) kept at temperatures ranging from 50° to 95° C.; the examples described herein employ second stage draw temperatures of 67° to 73° C. Draw ratios of up to 2X are applied in this second stage, but a ratio range of from 1.17X to 1.625X was employed in the examples. The fiber is passed through a water-wash, taken up on a spool, and dried. A set of hot rollers can be substituted for a portion or all of the glycerine draw bath. The resulting oriented filaments have good straight and knot tensile strengths.

Dimensional stability and in vivo tensile strength retention of the oriented filaments may be enhanced by subjecting the filaments to an annealing treatment. This optional treatment consists of heating the drawn filaments to a temperature of from about 40° to 95° C., most preferably from about 60° to 90° C. while restraining the filaments to prevent any substantial shrinkage. This process may begin with the filaments initially under tension or with up to 20% shrinkage allowed prior to restraint. The filaments are held at the annealing temperature for a few minutes to several days or longer depending on the temperature and processing conditions. In general, annealing at 60° to 90° C. for up to about 24 hours is satisfactory for the copolymers of the invention. Optimum annealing time and temperature for maximum fiber in vivo strength retention and dimensional stability is readily determined by simple experimentation for each fiber composition.

The filaments thus produced may be fabricated into sutures or ligatures, attached to surgical needles, packaged, and sterilized by known techniques.

The characteristic properties of the filaments of the invention are readily determined by conventional test procedures. The tensile properties (i.e., straight and knot tensile strengths, Young's Modulus, and elongation) displayed herein were determined with an INSTRON tensile tester. The settings used to determine the straight tensile, knot tensile, break elongation, and Young's Modulus were the following, unless indicated:

|  | Gauge Length (cm) | Chart Speed (cm/min) | Crosshead Speed (cm/min) |
| --- | --- | --- | --- |
| Straight Tensile | 12 | 20 | 10 |
| Knot Tensile | 5 | 10 | 10 |
| Break Elongation | 12 | 20 | 10 |
| Young's Modulus | 12 | 20 | 10 |

The straight tensile strength is calculated by dividing the force to break by the initial cross-sectional area of the fiber. The elongation at break is read directly from the stress-strain curve of the sample allotting 4-1/6% per centimeter of horizontal displacement.

Young's Modulus is calculated from the slope of the stress-strain curve of the sample in the linear elastic region as follows:

$$\text{Young's Modulus} = \frac{\tan\theta \times GL \times CS \times SL}{XH \times XS}$$

$\theta$ is the angle between the slope and the horizontal, XS is the initial cross-sectional area of the fiber, SL is the scale load, XH is the crosshead speed, CS is the chart speed, and GL is the gauge length. The SL may be selected to provide at $\theta$ close to 45°.

The knot tensile strength of a fiber is determined in separate experiments. The test article is tied into a surgeon's knot with one turn of the filament around flexible tubing of ¼ inch inside diameter and 1/16 inch wall thickness. The surgeon's knot is a square knot in which the free end is first passed twice, instead of once, through the loop, and the ends drawn taut so that a single knot is superimposed upon a compound knot. The first knot is started with the left end over the right end and sufficient tension is exerted to tie the knot securely.

The specimen is placed in the INSTRON tensile tester with the knot approximately midway between the clamps. The knot tensile strength is calculated by dividing the force required to break by the initial cross-sectional area of the fiber.

The tensile strength values and Young's modulus (Y.M.) are reported as KPSI, or PSI×10³.

EXAMPLES 3 AND 4

The copolymers described in Examples 1 and 2, respectively, were extruded into monofilament fibers by the procedure described above.

Both fibers were drawn a total of 6.5X in two stages, under the following conditions:

|  | Stage 1 | Stage 2 |
| --- | --- | --- |
| Example 3 | 5X(53° C.) | 1.3X(69° C.) |
| Example 4 | 4X(53° C.) | 1.625X(67° C.) |

Certain physical and in vitro strength properties of these drawn fibers, after annealing (70° C./8 hours/restrained from shrinking) are displayed in Table I.

TABLE I

|  | Examples | |
| --- | --- | --- |
|  | 3 | 4 |
| Diameter (mils) | 7.8 | 7.0 |
| Str. Tensile (KPSI) | 49 | 72 |
| Knot Tensile (KPSI) | 39 | 54 |
| Elong. (%) | 59 | 48 |
| Y.M. (KPSI) | 103 | 152 |
| % BSR (pH 7.26, Phosphate Buffer, 50° C.) In Vitro[1] |  |  |
| 4 Days | 66 | 67 |
| 7 Days | 54 | 45 |

[1]In vitro BSR = Breaking strength retention (% retention of initial tensile strength) after the indicated number of days in phosphate buffer at pH = 7.26 and 50° C.

EXAMPLE 5

Preparation of Polydioxanone-melt/L(−)Lactide at 90/10 initial weight composition (92.7/7.3 mole %)

A thoroughly dried mechanically stirred 1.5 gallon stainless steel reactor was charged with 1800 grams (17.632 moles) of p-dioxanone, 3.9 milliliters of 1-dodecanol, and 1.92 milliliters of stannous octoate (0.33 molar solution in toluene). The contents of the reactor were held under high vacuum at room temperature for about 16 hours. The reactor was purged with nitrogen. The reaction mixture was heated to 110° C. and maintained there for 5¼ hours. A sample of the polymer was removed (I.V.=0.54 dl/g, unreacted monomer content=25.5%) and 200 grams (1.3877 mole) of L(−)lactide was added. The temperature was raised to and maintained at around 125° C. for about 2 hours. The polymer was isolated, ground, and dried 48 hours/80° C./0.1 mm Hg. to remove any unreacted monomer. A weight loss of 22.3% was observed. The resulting polymer had a melting temperature of about 102° C. by hot stage microscopy, an inherent viscosity of 2.15 dl/g, a crystallinity content of about 33% by X-ray diffraction, and a PDO/PL molar ratio of 93.3/6.7 by NMR.

EXAMPLE 6

Preparation of Polydioxanone-melt/L(−)Lactide at 90/10 initial weight composition (92.7/7.3 mole %)

A thoroughly dried mechanically stirred 1.5 gallon stainless steel reactor was charged with 1800 gram (17.632 moles) of p-dioxanone, 3.9 milliliters of 1-dodecanol, and 1.92 milliliters of stannous octoate (0.33 molar solution in toluene). The contents of the reactor were held under high vacuum at room temperature for about 16 hours. The reactor was purged with nitrogen. The reaction mixture was heated to 110° C. and maintained there for 5½ hours. A sample of the polymer was removed (I.V.=1.37 dl/g, free monomer analysis, 18.4%) and 200 grams (1.3877 mole) of L(−)lactide was added. The temperature was raised to and maintained at around 125° C. for about 2 hours. The polymer was isolated, ground, and dried 48 hours/80° C./0.1 mm Hg. to remove any unreacted monomer. A weight loss of 28.1% was observed. The resulting polymer had a melting range of 98°–102° C. by hot stage microscopy, and an inherent viscosity of 1.85 dl/g.

EXAMPLES 7 AND 8

The copolymers described in Examples 5 and 6, respectively, were extruded into monofilament fibers. Certain physical properties of oriented and annealed fibers are shown in Table II, below. The orientation conditions were as follows:

|  | Stage 1 | Stage 2 | Total Draw Ratio |
|---|---|---|---|
| Example 7 | 5.5X(49° C.) | 1.27X(72° C.) | 7X |
| Example 8 | 5X(55° C.) | 1.4X(73° C.) | 7X |

The annealing conditions for both fibers were 12 hours at 60° C., restrained from shrinking.

TABLE II

| Fiber Properties (Natural)[2] | Example 7 | | Example 8 | |
|---|---|---|---|---|
|  | oriented | Annealed 12 h/ 60° C. | oriented | Annealed 12 h/ 60° C. |
| Diameter (mils) | 7.8 | 7.9 | 7.4 | 7.6 |
| Str. Tensile KPSI | 92 | 91 | 108 | 99 |
| Knot Tensile, KPSI | 45 | 48 | 46 | 47 |
| Elongation @ Break % | 65 | 38 | 62 | 42 |
| Young's Modulus KPSI | 85 | 143 | 88 | 181 |
| In Vitro BSR |  |  |  |  |
| 4 days/50° C. | — | 70% | — | 67% |
| 7 days/50° C. | — | — | — | 56% |
| In Vivo BSR[3] |  |  |  |  |
| 21 Days |  | 64% |  | 59% |
| 28 Days |  | 48% |  | 49% |
| 56 Days |  | 9% |  | 11% |
| In Vivo Absorption[4] |  |  |  |  |
| 91 Days |  | 69 |  | 73 |
| 119 Days |  | 30 |  | 68 |
| 154 Days |  | 0 |  | 0 |

[2]"Natural" means undyed.
[3]/[4]In vivo BSR and absorption are explained below.

Breaking Strength Retention In Vivo

The breaking strength retention (BSR) in vivo of a fiber is determined by implanting two strands of the fiber in the dorsal subcutis of each of a number of Long-Evans rats. The number of rats used is a function of the number of implantation periods, employing 4 rats per period giving a total of eight (8) examples for each of the periods. Thus 16, 24, or 32 segments of each fiber are implanted corresponding to two, three, or four implantation periods. The periods of in vivo residence are 7, 14, 21, or 28 days. The ratio of the mean value of 8 determinations of the breaking strength (determined with an INSTRON tensile tester employing the following settings: a gauge length of 1 inch, a chart speed of 1 inch/minute, and a crosshead speed of 1 inch/minute) at each period to the mean value (of 8 determinations) obtained for the fiber prior to implantation constitutes its breaking strength retention for that period.

In Vivo Absorption

The in vivo absorption test is carried out as follows:
Two 2-centimeter sections of the sample filaments are implanted into both the left and right gluteal muscles of two female rats for each period of the study. This procedure yields a potential total of 8 cross-sections per period, for periods of 5, 91, 119, 154 and 210 days.

The implants are recovered at the designated intervals and fixed in buffered formalin. Muscle cross-sections are made and stained with H&E and examined microscopically. Tissue reactions are evaluated, and the diameter of the remaining filament is determined. The filament diameter after 5 days is used as the 100% reference point for determining the percent cross sectional area remaining after the later periods.

EXAMPLE 9

Preparation of Polydioxanone-melt/L(—)Lactide at 90/10 initial weight composition (92.7/7.3 mole %)

A thoroughly dried mechanically stirred 1.5 gallon stainless steel reactor was charged with 1800 grams (17.632 moles) of p-dioxanone, 3.9 milliliters of 1-dodecanol, and 1.92 milliliters of stannous octoate (0.33 molar solution in toluene). The contents of the reactor were held under high vacuum at room temperature for about 16 hours. The reactor was purged with nitrogen. The reaction mixture was heated to 110° C. and maintained there for 5½ hours. A sample of the polymer was removed (I.V.=0.79 dl/g., free monomer=10.5%—this free monomer content analysis may have been in error, since it seems low) and 200 grams (1.3877 mole) of L(—)lactide was added. The temperature was raised to and maintained at around 125° C. for about 2 hours. The polymer was isolated, ground, and dried 48 hours/80° C./0.1 mm Hg. to remove any unreacted monomer. A weight loss of 22% was observed. The resulting polymer had a melting range of 102°–106° C. by hot stage microscopy, an inherent viscosity of 1.95 dl/g, and a PDO/PL molar ratio of 93.8/6.2 by NMR.

EXAMPLE 10

Preparation of Polydioxanone-melt/L(—)lactide at 90/10 initial weight composition (92.7/7.3 mol %) in a pilot plant size reactor A thoroughly dried mechanically stirred 10-gallon stainless steel "Helicone" reactor was charged, under nitrogen purge, with 8,950 grams (87.745 moles) of p-dioxanone, 9.55 milliliters of stannous octoate catalyst solution (0.33 molar solution in toluene), and 15.86 grams of 1-dodecanol. The contents of the reactor were held under a vacuum (1 mm of mercury or less) for 20 minutes. The vacuum was released with dry nitrogen and the contents were again subjected to a vacuum of at least 1 mm of mercury for an additional 20 minutes. The reactor was then purged with nitrogen. The reaction mixture was heated to 110° C. The polymerization time was 6 hours from the time the temperature reached 100° C. At the end of the six-hour first stage polymerization, (I.V.=1.20 dl/g, unreacted monomer=25.3%), 994 grams (6.903 moles) of L(—)lactide was added to the reactor under nitrogen purge. The temperature was raised to about 140° C. and was maintained there for 2 hours. After the two-hour period, the polymer was isolated, cooled, ground, sieved, and then dried in a 1 cubic foot vacuum tumble drier, under vacuum, for ten hours at ambient temperature (about 25° C.), then 12 hours at 60° C., and then 20 hours at 70° C., to remove any unreacted monomer(s). A summary of the polymer properties is presented in Table V, below.

The copolymers of Example 9 and 10 were extruded into monofilaments by melting at 130°–160° C. and pumping the melt through a 60-mil capillary die having a 5/1 mm length to diameter ratio. The extrudate was quenched by passage through a cold (i.e., up to room temperature) water bath and was then drawn in two stages. The first stage drawing was done on rolls at room temperature, and the second stage drawing included passing the filament through a heated oven. Some of the extrusion and drawing conditions are displayed below in Table III:

TABLE III

| | Example 9 | Example 10 |
|---|---|---|
| Block/Die Temp. °C. | 116/121 | 133/135 |
| 1st and 2nd Godet speed, feet/min. | 12 | 13 |
| 3rd Godet speed, feet/min. | 60 | 60 |
| Oven Temperature, °C. | 49 | 77 |
| 4th Godet speed, feet/min. | 75 | 85 |
| Total draw ratio | 6.3X | 6.5X |

The fibers were allowed to crystallize further overnight at room temperature, and then were redrawn in one stage through a heated oven. The total draw ratio varied from 1.20X to 1.33X, and the oven temperature was 82° C. After redrawing, the fibers were annealed under dry nitrogen for 6 hours with no relaxation at 90° C. The tensile properties of size 2/0 samples of the Example 9 and 10 fibers are displayed below in Table IV:

TABLE IV

| | Example 9 | Example 10 |
|---|---|---|
| Diameter, mils | 12.9 | 13.1 |
| Straight tensile, KPSI | 93 | 86 |
| Knot tensile, KPSI | 54 | 51 |
| Elongation, % | 49 | 54 |
| Young's Modulus, KPSI | 184 | 152 |

EXAMPLE 11

Preparation of D&C violet #2 dyed Polydioxanone-melt/L(−)lactide at 91/9 initial weight composition (93.4/6.6 mol %) in a pilot plant size reactor The polymer preparation procedure followed was similar to that described in Example 10, with the following differences:

Initial charge was 10,250 grams (100.49 moles) of p-dioxanone, 11.82 milliliters of stannous octoate catalyst solution, 16.35 grams of 1-dodecanol, and 10.25 grams of D&C violet #2 dye. At the end of the six-hour first stage polymerization (I.V.=1.14 dl/g, unreacted monomer=23.5%), 1025 grams (7.118 moles) of L(−)lactide was added. The polymer, after isolation, cooling, grinding, and sieving, was dried in a vacuum tumble drier for 10 hours at ambient temperature and then 32 hours at 70° C. A summary of the polymer properties is presented in Table V:

TABLE V

| | Example 10 | Example 11 |
|---|---|---|
| Inherent viscosity, dl/g | 2.02 | 1.82 |
| Tg, °C. (DSC) | −6 | −9 |
| Tm, °C. (DSC) | 104 | 110 |
| Crystallinity, % (X-ray diffraction) | 34 | 38 |
| PDO/PL Mol ratio, by NMR | 92.7/7.3 | 93.0/7.0 |

The copolymer of Example 11 was extruded into a monofilament in a manner similar to that described above for Examples 9 and 10. Some of the extrusion and drawing conditions for the production of size 2/0 fibers are shown below in Table VI:

TABLE VI

| Block/Die Temp., °C. | 132/133 |
|---|---|
| 1st and 2nd Godet speed, fpm | 13 |
| 3rd Godet speed, fpm | 60 |
| Oven Temperature, °C. | 77 |
| 4th Godet speed, fpm | 92 |
| Total draw ratio | 7.1X |

The fiber was allowed to crystallize further overnight at room temperature, and then was redrawn in one stage through a heated oven under conditions similar to those described above for Examples 9 and 10. After redrawing, the fibers were annealed under dry nitrogen at 90° C. with no relaxation for 6 hours. The annealed fiber tensile properties of this size 2/0 fiber are displayed below in Table VII:

TABLE VII

| Diameter, mils | 15.0 |
|---|---|
| Straight tensile, KPSI | 86 |
| Knot Tensile, KPSI | 51 |
| Elongation, % | 63 |
| Young's Modulus, KPSI | 192 |
| In vitro BSR (5 days/55° C./pH = 9.1) | 57.6% |

EXAMPLE 12

Preparation of Polydioxanone-melt/L(−)Lactide at 70/30 initial weight composition (76.7/23.3 mole %)

A thoroughly dried mechanically stirred 1.5 gallon stainless steel reactor was charged with 1400 grams (13.7137 moles) of p-dioxanone, 0.77 milliliter of diethylene glycol, 1.81 milliliters of stannous octoate (0.33 molar solution in toluene), and 1.0 gram of D&C violet #2. The contents of the reaction flask were held under high vacuum at room temperature for about 16 hours. The reactor was purged and vented with nitrogen. The reaction mixture was heated to 110° C. and maintained there for 6 hours. A sample of the polymer was removed (for I.V. and free monomer content analysis) and 600 grams (4.1631 moles) of L(−)lactide was added. The temperature was raised to, and maintained at, around 135° C. for about 2 hours. The polymer was isolated, ground, and dried to remove any unreacted monomers. A weight loss of 27.3% was observed. The resulting polymer had a melting range of 98°–104° C. (by hot melt microscopy) at 25% crystallinity, an inherent viscosity of 2.44 dl/g, and a PDO/PL mol ratio of 83.6/16.4 by NMR.

EXAMPLE 13

Preparation of Polydioxanone-melt/L(−)Lactide at 93/7 by weight (95/5 by mole %)

A thoroughly dried mechanically stirred 1.5 gallon stainless steel reactor was charged with 1860 grams (18.2196 moles) of p-dioxanone, 3.93 milliliters of 1-dodecanol, 1.94 milliliters of stannous octoate (0.33 molar solution in toluene), and 1.0 gram of D&C violet #2. The contents of the reactor were held under high vacuum at room temperature for about 16 hours. The reactor was purged and vented with nitrogen. The reaction mixture was heated to 110° C. and maintained there for 6 hours. A sample of the polymer was removed (I.V.=1.88 dl/g, free monomer content=19.2%) and 140 grams (0.9714 mole) of L(−)lactide was added. The temperature was raised to, and maintained at, 125°–135° C. for about 2 hours. The polymer was isolated, ground, and dried to remove any unreacted monomers. A weight loss of 24.2% was observed. The resulting polymer had a melting range of 100°-106° C. by hot melt microscopy, a crystallinity of 26%, and an inherent viscosity of 2.09 dl/g.

Properties of Fibers from Examples 12 and 13

The copolymers described in Examples 12 and 13 were extruded, drawn, and redrawn into monofilament fibers in a manner similar to that described above for Examples 9 to 11. The redrawn fibers were annealed 6 hours at 90° C. with no relaxation (under nitrogen). The tensile properties of these fibers were the following:

TABLE VIII

|  | Example 12 | Example 13 |
| --- | --- | --- |
| Diameter, mils | 13.7 | 13.6 |
| Straight tensile, KPSI | 78 | 96 |
| Knot tensile, KPSI | 43.4 | 50 |
| Elongation, % | 34 | 33 |
| Young's Modulus, KPSI | 331 | 253 |

EXAMPLE 14

Preparation of Polydioxanone-melt/L(—)Lactide at 93/7 by weight (95/5 by mole %)

A thoroughly dried mechanically stirred 1.5 gallon stainless steel reactor was charged with 1860 grams (18.2196 moles) of p-dioxanone, 1.09 milliliters of diethylene glycol, 1.94 milliliters of stannous octoate (0.33 molar solution in toluene), and 1.0 gram of D&C violet #2. The contents of the reactor were held under high vacuum at room temperature for about 16 hours. The reactor was purged and vented with nitrogen. The reaction mixture was heated to 110° C. and maintained there for 6 hours. A sample of the polymer was removed (I.V.=2.34 dl/g, free monomer=21.5%) and 140 grams (0.9714 mole) of L(—)lactide was added. The temperature was raised to, and maintained at, 125°-135° C. for about 2 hours. The polymer was isolated, ground, and dried to remove any unreacted monomers. A weight loss of 24% was observed. The resulting polymer had a melting range of 97°-103° C. by hot stage microscopy, and an inherent viscosity of 2.65 dl/g.

EXAMPLE 15

Preparation of Polydioxanone-melt/D,L-Lactide at 70/30 initial composition (76.7/23.3 mole %)

A flame dried, 250 milliliter, round bottom, two-neck flask was charged with 70 grams (0.6862 mole) of p-dioxanone, 0.182 milliliter of 1-dodecanol, and 0.090 milliliter of stannous octoate (0.33 molar solution in toluene). The contents of the reaction flask were held under high vacuum at room temperature for about 16 hours.

The flask was fitted with a flame dried mechanical stirrer and an adaptor with a hose connection. The reactor was purged with nitrogen three times before being vented with nitrogen. The reaction mixture was heated to 110° C. and maintained there for 6 hours. To the reaction flask, 30 grams (0.2081 mole) of D,L-lactide was added and the temperature was raised to 140° C. and maintained there for 2 hours. The polymer was isolated, ground, and dried at 60°-80° C./64 Hrs/0.1 mm Hg. to remove unreacted monomers. A weight loss of 29.6% was observed. The resulting polymer had a melting range of 98°-102° C., and an inherent viscosity of 1.69 dl/g.

The copolymer described in Example 15 was extruded into monofilament fibers. The physical properties of drawn and annealed (6 hrs/90° C.) fibers are shown in Table IX.

TABLE IX

| Example 15 | | |
| --- | --- | --- |
| Initial composition of PDO-melt/D,L-lactide | 70/30 by weight % 76.7/23.3 by mole % | |
| I.V. dl/g | 1.69 | |
| Tm | 108° C. (DSC) | |
| Tg | −7.5° C. (DSC) | |
| Crystallinity | 29% | |
| Fiber Properties (annealed 6 hrs/90° C./ no shrinkage) | Size 2/0 | Size 4/0 |
| Diameter (mils) | 13.36 | 7.73 |
| Straight Tensile, KPSI | 59 | 78 |
| Knot Tensile, KPSI | 39 | 50 |
| Elongation, % | 60 | 42 |
| Young's Modulus, KPSI | 203 | 248 |

It is probable that the subject copolymers comprise long blocks of polymerized p-dioxanone, which are crystallizable, with shorter segments containing random sequences of polymerized p-dioxanone and lactide. These shorter segments are essentially non-crystallizable, which accounts for the fact that the copolymers of this invention have a slightly lower degree of crystallization than the p-dioxanone homopolymer.

NMR analyses of the copolymers of the invention indicate that the comonomers are chemically linked therein. X-ray analyses of the copolymers indicate the presence of poly(p-dioxanone) crystallinity. It also indicates the presence of long enough segments or blocks to give rise to crystallinity. The results of these two analytical techniques support the view that the polymers of the invention are not random copolymers. Random copolymers are known to be essentially non-crystalline. Gel permeation chromatography data also support the view that the subject copolymers do not comprise blends of two or more distinct polymers.

Based on the foregoing discussion the segmented copolymers of the invention may be characterized as follows:

Contain from about 70 to about 98 weight percent polymerized p-dioxanone, the remainder being co-polymerized lactide. For the preferred suture utility, the copolymers contain from about 90 to 97 mol percent co-polymerized p-dioxanone, the remainder being polymerized lactide.

In the natural (undyed) state, the copolymer has a melting temperature, by differential scanning calorimetry or hot stage microscopy, of from about 90° to about 110° C. (the addition of dye may raise the melting temperature by as much as about 5° C.);

In the molten state, by optical microscopy, the copolymer has a single phase;

By X-ray diffraction analysis, the copolymer has a crystallinity of from about 20 to about 45 percent; and By gel permeation chromatography, the copolymer shows only a single peak in the molecular weight distribution curve.

The subject copolymers can be made having inherent viscosities from about 1.6 to about 2.7, and are preferably made having IV's of from about 1.9 to about 2.2. As a general rule, it is difficult to process p-dioxanone homopolymers into fibers if such homopolymers have I.V.'s greater than about 1.95. Therefore, this invention provides a means for providing p-dioxanone polymer fibers of higher molecular weight than has been heretofore available. The copolymers of this invention appear to be more thermally stable than p-dioxanone homopolymer.

Drawn and annealed monofilaments, from which surgical sutures and ligatures are made, made from the copolymers of the invention are usually more pliable than comparably sized monofilament fibers made from p-dioxanone homopolymer. At the same time, the monofilament fibers of the subject invention usually have equal or higher strength than the monofilament fibers made from the homopolymer. This advantageous combination of properties is illustrated by the following Example 16:

EXAMPLE 16

By a procedure analogous to that described in Example 5, above, a copolymer was made from p-dioxanone and L(−)lactide in molar proportions of 95/5. The resulting polymer had a melting range of 99°–100° C. by hot stage microscopy, an I.V. of 2.17 dl/g, a percent crystallinity of about 28 by X-ray diffraction, and a PDO/PL molar ratio of 95/5 by NMR.

The copolymer was extruded and drawn into monofilaments by a procedure analogous to those described above. The drawing conditions were as follows:

| 1st stage draw | 4x at 47° C. |
| 2nd stage draw | 1.6875x at 69° C. |
| Total draw ratio | 6.75x |

The drawn monofilaments were annealed 6 hours at 80° C., with a 5% relaxation. Representative properties of the drawn and annealed monofilaments are displayed in Table X, below, along with properties of typical commercial p-dioxanone homopolymer drawn and annealed under similar conditions;

TABLE X

| | Example 16 | | Homopolymer Control-Drawn and Annealed |
|---|---|---|---|
| | Drawn | Drawn and Annealed | |
| Diameter, mils | 7.0 | 7.6 | 7–8 |
| Str. Tensile, KPSI | 100 | 87 | 81 |
| Knot Tensile, KPSI | 55 | 54 | 52 |
| Elongation, % | 56 | 50 | 49 |
| Youngs Modulus, KPSI | 137 | 169 | 271 |

The properties of monofilaments produced from the copolymers of the invention are dependent upon a number of factors, such as PDO/PL ratio, molecular weight, drawing and annealing conditions, and the like. As a general rule, however, drawn and annealed monofilament fibers made from the preferred copolymers (which have PDO/PL mol ratios of from about 90/10 to about 97/3), will exhibit the following properties:

| Straight tensile, KPSI | 70–110 |
| Knot Tensile, KPSI | 40–70 |
| Elongation, percent | 30–65 |
| Young's Modulus KPSI | 100–250 |
| In vivo BSR, 3 weeks | 50–70% |
| 4 weeks | 40–50% |
| 8 weeks | 5–15% |
| In vivo Absorption, to zero | less than 5 to 6 months |

What is claimed is:

1. Process for producing a crystalline copolymer of p-dioxanone and lactide which comprises subjecting a mixture of p-dioxanone homopolymer, p-dioxanone monomer, and lactide to an elevated temperature for a period of time sufficient to produce a crystalline copolymer of p-dioxanone and lactide.

2. Process of claim 1 which comprises the steps of:
    (a) polymerizing p-dioxanone monomer in the presence of a catalytically effective amount of a polymerization catalyst and an initiator to produce a first mixture of p-dioxanone homopolymer and p-dioxanone monomer; and
    (b) adding lactide to said first mixture to produce a second mixture, and subjecting said second mixture to an elevated temperature for a period of time sufficient to produce a crystalline copolymer of p-dioxanone and lactide.

3. The process of claim 2 wherein said first mixture contains from about 15 to 30 weight percent p-dioxanone monomer, based on total weight of said first mixture.

4. The process of claim 2 wherein the lactide is employed in an amount of from about 2 to about 30 weight percent, based on total weight of p-dioxanone and lactide charged in steps (a) and (b).

5. The process of claim 2 wherein step (b) is carried out at a temperature of from about 110° C. to about 160° C.

6. A crystalline copolymer of p-dioxanone and lactide produced by the process of claim 1.

7. A crystalline copolymer of p-dioxanone and lactide produced by the process of claim 2.

8. A crystalline copolymer of p-dioxanone and lactide produced by the process of claim 3.

9. A copolymer of p-dioxanone and lactide containing from about 70 to about 98 weight percent polymerized p-dioxanone, the remainder being co-polymerized lactide, said copolymer being characterized as follows:
    an inherent viscosity of from about 1.6 to 2.7;
    a melting point of about 90° to about 110° C.;
    a crystallinity of about 20 to about 45 percent;
    a single peak in the molecular weight distribution curve;
    and, single phase in the molten state, by optical microscopy 10. The copolymer of claim 9 containing from about 90 to 97 mol percent polymerized p-dioxanone, the remainder being co-polymerized lactide.

11. A drawn and oriented filament comprising the copolymer of claim 10.

12. The filament of claim 11 in the form of a monofilament.

13. The filament of claim 12 in the form of a sterile surgical suture.

14. The monofilament of claim 12 having the following properties:

| straight tensile strength | 70–110 kpsi |
| knot tensile strength | 40–70 kpsi |
| elongation | 30–65% |
| Young's modulus | 100–250 kpsi |
| In vivo BSR, 3 weeks | 50–70% |
| 4 weeks | 40–50% |
| 8 weeks | 5–15% |
| In vivo absorption, to zero | less than 5 to 6 months |

15. The sterile surgical suture of claim 13 attached to a needle.

16. A surgical device comprising the crystalline copolymer of claim 9.